(12) United States Patent
Miller

(10) Patent No.: US 10,690,553 B1
(45) Date of Patent: Jun. 23, 2020

(54) VAPORIZABLE SUBSTANCE APPLICATION TOOL HAVING AN INTEGRATED IDEAL TEMPERATURE INDICATOR

(71) Applicant: Zachary Miller, Las Vegas, NV (US)

(72) Inventor: Zachary Miller, Las Vegas, NV (US)

(73) Assignee: ALL ZACK EVERYTHING LLC, Las Vegas, NV (US)

( * ) Notice: Subject to any disclaimer, the term of this patent is extended or adjusted under 35 U.S.C. 154(b) by 0 days.

(21) Appl. No.: 16/455,815

(22) Filed: Jun. 28, 2019

(51) Int. Cl.
| | |
|---|---|
| *G01K 13/02* | (2006.01) |
| *A24F 47/00* | (2020.01) |
| *A61M 15/00* | (2006.01) |
| *G01K 11/16* | (2006.01) |
| *G01K 7/04* | (2006.01) |

(52) U.S. Cl.
CPC ............ *G01K 13/02* (2013.01); *A24F 47/00* (2013.01); *A61M 15/0001* (2014.02); *G01K 7/04* (2013.01); *G01K 11/16* (2013.01); *A61M 2205/3368* (2013.01); *A61M 2205/583* (2013.01); *G01K 2013/024* (2013.01)

(58) Field of Classification Search
CPC .. A24F 1/30; A24F 1/00; A24F 47/008; A24F 1/32; A24F 47/00; A24F 42/60; A24F 47/004; A61M 15/06; A61M 2205/3368; A61M 15/08; A61M 16/0051; A61M 16/0078; A61M 16/204; A61M 2205/18; A61M 35/003; A61M 15/0001; A61M 15/0065; A61M 15/0086; A61M 11/041; A61M 11/048; A61M 15/00; A61K 2300/00; A61K 31/192

USPC ............ 374/141, 162; 116/216; 128/201.21, 128/203.12
See application file for complete search history.

(56) References Cited

U.S. PATENT DOCUMENTS

| | | |
|---|---|---|
| 2,035,334 A | 3/1936 | Monrad |
| 2,898,845 A | 8/1959 | Dight |
| 3,504,544 A | 4/1970 | Tymkewicz |

(Continued)

FOREIGN PATENT DOCUMENTS

| | | |
|---|---|---|
| CN | 102106677 A | 6/2011 |
| CN | 103300833 A | 9/2013 |

(Continued)

*Primary Examiner* — Gail Kaplan Verbitsky
(74) *Attorney, Agent, or Firm* — Legalforce RAPC Worldwide

(57) ABSTRACT

Disclosed is a vaporizable substance application tool having an integrated ideal temperature indicator. In one embodiment, an apparatus includes an applicator, a thermocouple, and a temperature indicator. The applicator is positioned on a first end of the apparatus to apply a vaporizable substance onto a heatable surface. The thermocouple is positioned on a second end of the apparatus. The temperature indicator is positioned between the applicator and the thermocouple. In addition, the temperature indicator of the apparatus visually indicates different temperature states. In a first state, a background of the temperature indicator illuminates in a first color when the temperature is below an ideal range. In a second state, the background of the temperature indicator illuminates in a second color when the temperature is within the ideal range. In a third state, the background of the temperature indicator illuminates in a third color when the temperature exceeds the ideal range.

20 Claims, 7 Drawing Sheets

(56) References Cited

U.S. PATENT DOCUMENTS

| | | | |
|---|---|---|---|
| 3,552,210 A | 1/1971 | Wright, Jr. | |
| 3,695,110 A | 10/1972 | Biolik | |
| 3,762,896 A * | 10/1973 | Borst | C03B 37/048 65/384 |
| 4,083,250 A | 4/1978 | Goff et al. | |
| 4,519,778 A * | 5/1985 | von Burg | D02J 13/00 122/504.1 |
| 4,878,588 A | 11/1989 | Ephraim | |
| 5,024,622 A | 6/1991 | Ide | |
| 5,575,563 A | 11/1996 | Chiu et al. | |
| 5,829,878 A | 11/1998 | Weiss et al. | |
| 5,923,258 A | 7/1999 | Tseng | |
| 6,000,845 A | 12/1999 | Tymkewicz et al. | |
| 6,065,391 A | 5/2000 | Archard et al. | |
| 6,090,050 A | 7/2000 | Constantinides | |
| 6,412,398 B1 | 7/2002 | Norcross et al. | |
| 6,772,756 B2 | 8/2004 | Shayan | |
| 7,083,347 B2 | 8/2006 | Marcotte et al. | |
| 7,275,866 B2 | 10/2007 | Tseng | |
| 7,350,973 B2 | 4/2008 | Craig et al. | |
| 7,520,668 B2 | 4/2009 | Chen | |
| 7,633,404 B2 | 12/2009 | Tseng | |
| 7,854,550 B2 | 12/2010 | Chan et al. | |
| 7,997,280 B2 | 8/2011 | Rosenthal | |
| 8,038,346 B2 | 10/2011 | Hsieh | |
| 8,235,591 B2 | 8/2012 | Harris | |
| 8,910,630 B2 * | 12/2014 | Todd | A61M 11/042 128/203.12 |
| 9,552,706 B2 * | 1/2017 | Schneider, II | G08B 5/36 |
| 10,182,596 B2 * | 1/2019 | Bagwell | A24F 1/30 |
| 10,244,793 B2 | 4/2019 | Monsees et al. | |
| 10,448,673 B2 * | 10/2019 | Gill | A24F 47/008 |
| 10,543,323 B2 * | 1/2020 | Buchberger | A61M 11/041 |
| 2001/0040911 A1 | 11/2001 | Rubenstein | |
| 2004/0211418 A1 * | 10/2004 | Shayan | A61M 11/041 128/203.12 |
| 2004/0247015 A1 | 12/2004 | Wojan et al. | |
| 2007/0086508 A1 | 4/2007 | Reading et al. | |
| 2008/0075143 A1 | 3/2008 | Lampke-Honeyghan et al. | |
| 2008/0075144 A1 | 3/2008 | Tseng | |
| 2009/0284380 A1 | 11/2009 | Chen et al. | |
| 2010/0123753 A1 | 5/2010 | Claypool et al. | |
| 2010/0126516 A1 * | 5/2010 | Yomtov | A24F 1/30 131/173 |
| 2013/0087144 A1 * | 4/2013 | Todd | A61B 5/1171 128/203.14 |
| 2013/0233309 A1 * | 9/2013 | Todd | A61B 5/1171 128/200.14 |
| 2014/0044147 A1 | 2/2014 | Wyatt | |
| 2015/0211941 A1 | 7/2015 | Roth | |
| 2015/0359263 A1 * | 12/2015 | Bellinger | H05B 1/0244 392/394 |
| 2016/0345631 A1 | 12/2016 | Monsees et al. | |
| 2017/0079331 A1 | 3/2017 | Monsees et al. | |
| 2017/0135408 A1 * | 5/2017 | Cameron | A24F 47/008 |
| 2018/0252592 A1 | 9/2018 | Charoonsophonsak et al. | |
| 2018/0304032 A9 * | 10/2018 | Trzecieski | A24F 47/00 |
| 2018/0369523 A1 * | 12/2018 | Pratt, Jr. | A61M 16/0078 |
| 2019/0223510 A1 * | 7/2019 | Bowen | A24D 1/14 |
| 2019/0224430 A1 * | 7/2019 | Raichman | A24F 47/008 |
| 2019/0261686 A1 * | 8/2019 | Bowen | A61M 15/0035 |

FOREIGN PATENT DOCUMENTS

| | | |
|---|---|---|
| CN | 204115880 U | 1/2015 |
| CN | 104586193 A | 5/2015 |
| CN | 204723034 U | 10/2015 |
| CN | 105411324 A | 3/2016 |
| CN | 205410714 U | 8/2016 |
| DE | 102009016273 A1 | 10/2010 |
| KR | 100554557 B1 | 3/2006 |
| WO | 2000003634 A1 | 1/2000 |
| WO | 2005036116 A2 | 4/2005 |
| WO | 2007002609 A2 | 1/2007 |
| WO | 2007047821 A1 | 4/2007 |
| WO | 2008056199 A1 | 5/2008 |
| WO | 2013025921 A1 | 2/2013 |
| WO | 2015192084 A1 | 12/2015 |

* cited by examiner

VAPORIZABLE SUBSTANCE APPLICATION TOOL HAVING AN INTEGRATED IDEAL TEMPERATURE INDICATOR

FIELD OF TECHNOLOGY

This disclosure relates generally to a substance application tool and, more particularly, to a vaporizable substance application tool having an integrated ideal temperature indicator.

BACKGROUND

Modern and alternative medicine may utilize vaporization processes for medicinal and/or therapeutic treatment of patients. In addition, lawful uses of vaporization processes may involve heating of substances (e.g., plant resins, botanical oils, essential oils) to ideal temperatures prior to inhalation by a user for religious beliefs and for lawful recreational purposes. For example, lawful recreational uses of vaporization techniques are growing in popularity for their ritualistic, therapeutic, and social benefits. The term "dabbing" has evolved to define a subcultural trend of socially inhaling a vaporizable substance (e.g., medicinal plant resin, a botanical and/or essential oil). The common way to "dab" is to heat a surface made of quartz, ceramic, and/or titanium (e.g., sub-culturally called a 'banger' and/or 'nail') using a flame.

The user may need to use a stop-watch and/or their smartphone timer to ensure that the heated surface is not exceedingly hot and/or cold prior to applying vaporizable substance to the heated surface. This may be cumbersome and inexact. Particularly, time is not the best measure of whether a surface is too hot and/or too cold. If the extracts are applied on an exceedingly hot surface, there may be a possibility of combustion of the vaporizable substance, creating a fire and/or burning of the vaporizable substance. Further, if extracts are applied to the surface on a surface which is too cold, the extracts may not vaporize and may need to be manually removed until the surface is adequately heated.

A subculture rule of thumb may involve heating of the surface for 30 seconds and then cooled for 60 seconds. A stopwatch may be used to measure 30 seconds when a flame is exposed to the surface using a blow torch, followed by 60 seconds waiting time during the cool down period. However, a room temperature, a variable thickness of the heated surface, an intensity of the flame, the distance of the blow torch from the heated surface, etc. may affect the precision of this estimation method.

An electronic nail (e.g., E-nails) may be used to maintain the consistent temperature of the surface to enable the user to inhale at a pre-set temperature. However, the electronic nail may not fit on different glass apparatuses. The electronic nail may be powered through a wall outlet, making the user immobile. However, the electronic nail may not allow the temperature to decline; therefore the constant temperature of the heated surface may create an unnatural experience to the user. In addition, the constant heat provided to the glass water pipe through the electronic nail may cause the water pipe to weaken over time, ultimately leading to breakage.

SUMMARY

Disclosed is a vaporizable substance application tool having an integrated ideal temperature indicator.

In one aspect, an apparatus includes an applicator, a thermocouple, and a temperature indicator. The applicator is positioned on a first end of the apparatus to apply a vaporizable substance onto a heatable surface. The thermocouple is positioned on a second end of the apparatus. The temperature indicator is positioned between the applicator and the thermocouple.

In addition, the temperature indicator of the apparatus visually indicates different temperature states. In a first state, a background of the temperature indicator illuminates in a first color when the temperature is below an ideal range. In a second state, the background of the temperature indicator illuminates in a second color when the temperature is within the ideal range. In a third state, the background of the temperature indicator illuminates in a third color when the temperature exceeds the ideal range.

Further, the vaporizable substance may be a plant resin, a botanical oil, and/or an essential oil. The ideal range may be approximately between 540 degrees Fahrenheit and 600 degrees Fahrenheit to correspond with an ideal heatable range of the vaporizable substance. The first color may be blue. The second color may be green. The third color may be red. The applicator may be removable from a measurement section of the apparatus. The measurement section may be comprised of the temperature indicator and the thermocouple. Different types of applicators may be attachable to the measurement section of the apparatus.

The apparatus may further include a short-range communication circuitry in the measurement section to communicate a usage data of the apparatus to a mobile device communicatively coupled with the apparatus. The usage data may be a frequency of use of the apparatus, a temperature measured at the time of application of the vaporizable substance onto the heatable surface using the applicator, and/or a temperature decay pattern during each use.

In addition, the apparatus may further include a haptic indicator and a chime indicator. The haptic indicator may enable the apparatus to vibrate when the temperature is in the ideal range. The chime indicator may make an audible noise when the temperature is in the ideal range. The chime indicator may be programmable with a ringtone and/or an audio clip when paired to the mobile device through the short-range communication circuitry.

In another aspect, a dabbing tool includes an applicator, a thermocouple, and a temperature indicator. The applicator is positioned on a first end of the dabbing tool to apply a vaporizable substance onto a banger. The vaporizable substance is a plant resin, a botanical oil, and/or an essential oil. The thermocouple is positioned on a second end of the dabbing tool. The temperature indicator is positioned between the applicator and the thermocouple.

The temperature indicator visually indicates different temperature states. In a first state, a background of the temperature indicator illuminates in a first color when the temperature is below an ideal range. In a second state, the background of the temperature indicator illuminates in a second color when the temperature is within the ideal range. In a third state, the background of the temperature indicator illuminates in a third color when the temperature exceeds the ideal range. The ideal range is approximately between 540 degrees Fahrenheit and 600 degrees Fahrenheit to correspond with an ideal heatable range of the vaporizable substance.

In yet another aspect, an apparatus includes an applicator, a thermocouple, and a temperature indicator. The applicator is positioned on a first end of the apparatus to apply a vaporizable substance onto a heatable surface. The thermocouple is positioned on a second end of the apparatus. The temperature indicator is positioned between the applicator and the thermocouple.

In addition, the temperature indicator of the apparatus visually indicates different temperature states. In a first state, a background of the temperature indicator illuminates in a first color when the temperature is below an ideal range. In a second state, the background of the temperature indicator illuminates in a second color when the temperature is within the ideal range. In a third state, the background of the temperature indicator illuminates in a third color when the temperature exceeds the ideal range.

Further, the ideal range is approximately between 540 degrees Fahrenheit and 600 degrees Fahrenheit to correspond with an ideal heatable range of the vaporizable substance. The applicator is removable from a measurement section of the apparatus. The measurement section is comprised of the temperature indicator and the thermocouple.

The methods and systems disclosed herein may be implemented in any means for achieving various aspects, and may be executed in a form of a non-transitory machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Figure 1A:
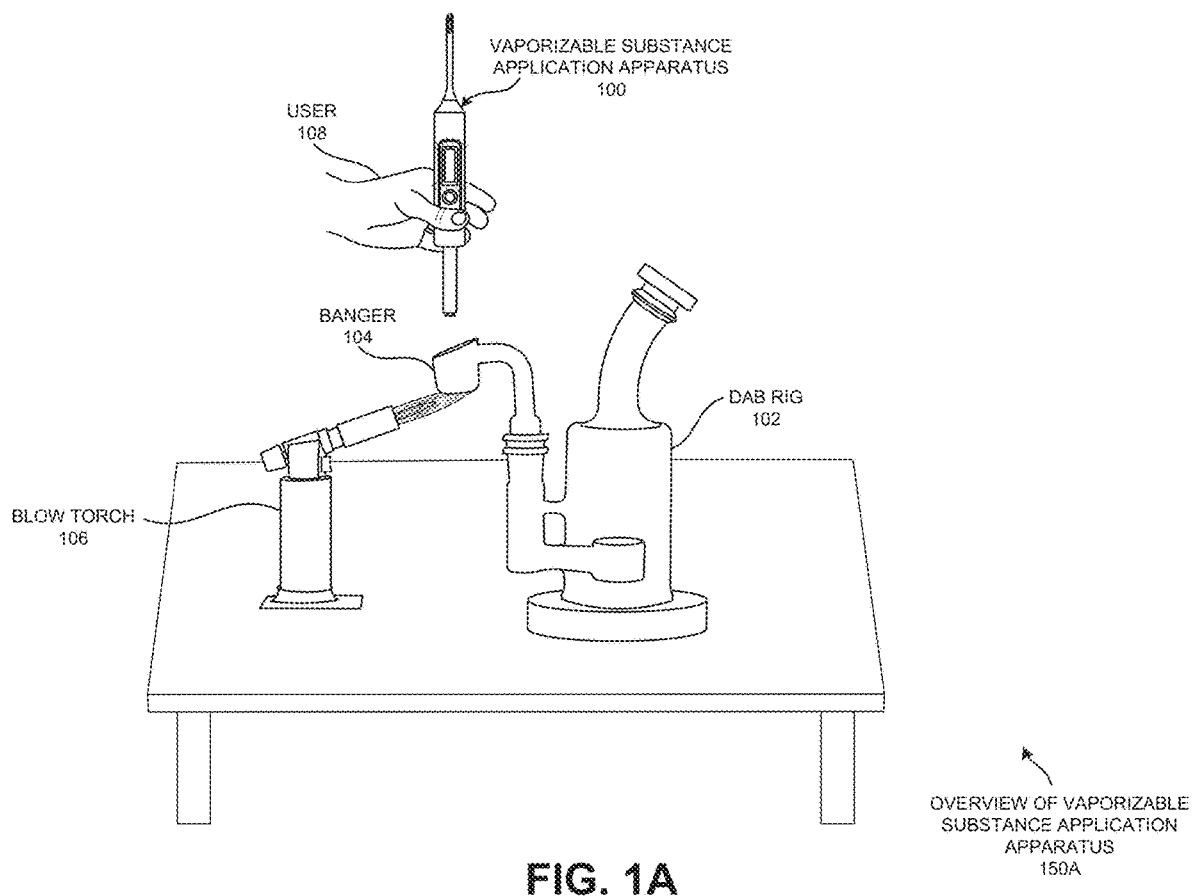
FIG. 1A is an overview of a vaporizable substance application apparatus to enable a user to observe an optimal temperature of a banger for inhaling a vaporizable substance, according to one or more embodiments.

Other features of the present embodiments will be apparent from the accompanying drawings and from the detailed description that follows.

DETAILED DESCRIPTION

Disclosed is a vaporizable substance application tool 100 having an integrated ideal temperature indicator 114. In one embodiment, an apparatus (e.g., vaporizable substance application tool 100 and/or dabbing tool) includes an applicator 116, a thermocouple 112, and a temperature indicator 114. The applicator 116 is positioned on a first end 111A of the apparatus 100 to apply a vaporizable substance 202 onto a heatable surface (e.g., banger 104 and/or heated surface 200). The thermocouple 112 is positioned on a second end 111B of the apparatus 100. The temperature indicator 114 is positioned between the applicator 116 and the thermocouple 112.

In addition, the temperature indicator 114 of the apparatus 100 visually indicates different temperature states. In a first state 400, a background (e.g., of display module 300) of the temperature indicator 114 illuminates in a first color (e.g., blue) when the temperature is below an ideal range (e.g., ideal state 402). In a second state (e.g., ideal state 402), the background (e.g., of display module 300) of the temperature indicator 114 illuminates in a second color (e.g., green) when the temperature is within the ideal range (e.g., ideal state 402). In a third state 404, the background (e.g., of display module 300) of the temperature indicator 114 illuminates in a third color (e.g., red) when the temperature exceeds the ideal range (e.g., ideal state 402), according to one embodiment.

Further, the vaporizable substance 202 may be a plant resin, a botanical oil, and/or an essential oil. The ideal range (e.g., ideal state 402) may be approximately between 540 degrees Fahrenheit and 600 degrees Fahrenheit to correspond with an ideal heatable range of the vaporizable substance 202. The first color may be blue. The second color may be green. The third color may be red. The applicator 116 may be removable from a measurement section 110 of the apparatus 100. The measurement section 110 may be comprised of the temperature indicator 114 and the thermocouple 112. Different types of applicators (e.g., applicator 116) may be attachable to the measurement section 110 of the apparatus 100, according to one embodiment.

The apparatus 100 may further include a short-range communication circuitry 308 in the measurement section 110 to communicate a usage data of the apparatus 100 to a mobile device 500 communicatively coupled with the apparatus 100. The usage data may be a frequency of use of the apparatus 100, a temperature measured at the time of application of the vaporizable substance 202 onto the heatable surface (e.g., banger 104 and/or heated surface 200) using the applicator 116, and/or a temperature decay pattern during each use, according to one embodiment.

In addition, the apparatus 100 may further include a haptic indicator 304 and a chime indicator 306. The haptic indicator 304 may enable the apparatus 100 to vibrate when the captured temperature is in the ideal range (e.g., ideal state 402). The chime indicator 306 may make an audible noise when the captured temperature is in the ideal range (e.g., ideal state 402). The chime indicator 306 may be programmable with a ringtone and/or an audio clip when paired to the mobile device 500 through the short-range communication circuitry 308, according to one embodiment.

In another embodiment, a dabbing tool (e.g., vaporizable substance application tool 100) includes an applicator 116, a thermocouple 112, and a temperature indicator 114. The applicator 116 is positioned on a first end 111A of the dabbing tool (e.g., vaporizable substance application tool 100) to apply a vaporizable substance 202 onto a banger 104. The vaporizable substance 202 is a plant resin, a botanical oil, and/or an essential oil. The thermocouple 112 is positioned on a second end 111B of the dabbing tool (e.g., vaporizable substance application tool 100). The temperature indicator 114 is positioned between the applicator 116 and the thermocouple 112.

The temperature indicator 114 visually indicates different temperature states. In a first state 400, a background (e.g., of display module 300) of the temperature indicator 114 illuminates in a first color (e.g., blue) when the temperature is below an ideal range (e.g., ideal state 402). In a second state (e.g., ideal state 402), the background (e.g., of display module 300) of the temperature indicator 114 illuminates in a second color (e.g., green) when the temperature is within the ideal range (e.g., ideal state 402). In a third state 404, the background (e.g., of display module 300) of the temperature indicator 114 illuminates in a third color (e.g., red) when the temperature exceeds the ideal range (e.g., ideal state 402). The ideal range (e.g., ideal state 402) is approximately between 540 degrees Fahrenheit and 600 degrees Fahrenheit to correspond with an ideal heatable range of the vaporizable substance 202, according to one embodiment.

In yet another embodiment, an apparatus (e.g., vaporizable substance application tool 100 and/or dabbing tool) includes an applicator 116, a thermocouple 112, and a temperature indicator 114. The applicator 116 is positioned on a first end 111A of the apparatus 100 to apply a vaporizable substance 202 onto a heatable surface (e.g., banger 104 and/or heated surface 200). The thermocouple 112 is positioned on a second end 111B of the apparatus 100. The temperature indicator 114 is positioned between the applicator 116 and the thermocouple 112.

In addition, the temperature indicator 114 of the apparatus 100 visually indicates different temperature states. In a first state 400, a background (e.g., of display module 300) of the temperature indicator 114 illuminates in a first color (e.g., blue) when the temperature is below an ideal range (e.g., ideal state 402). In a second state (e.g., ideal state 402), the background (e.g., of display module 300) of the temperature indicator 114 illuminates in a second color (e.g., green) when the temperature is within the ideal range (e.g., ideal state 402). In a third state 404, the background (e.g., of display module 300) of the temperature indicator 114 illuminates in a third color (e.g., red) when the temperature exceeds the ideal range (e.g., ideal state 402), according to one embodiment.

Further, the ideal range (e.g., ideal state 402) is approximately between 540 degrees Fahrenheit and 600 degrees Fahrenheit to correspond with an ideal heatable range of the vaporizable substance 202. The applicator 116 is removable from a measurement section 110 of the apparatus 100. The measurement section 110 is comprised of the temperature indicator 114 and the thermocouple 112, according to one embodiment.

FIG. 1A is an overview 150A of a vaporizable substance application apparatus 100 to enable a user 108 to observe an optimal temperature (e.g., ideal state 402) of a banger (e.g., banger 104 and/or heated surface 200) for inhaling a vaporizable substance 202, according to one embodiment. Particularly, FIG. 1A illustrates a vaporizable substance application apparatus 100, a dab rig 102, a banger 104, a blow torch 106, and a user 108, according to one embodiment.

The vaporizable substance application apparatus 100 (e.g., dabbing tool) may be an extract (e.g., vaporizable substance 202) applicator tool (e.g., applicator 116) with an integrated temperature indicator 114. The vaporizable substance application apparatus 100 may visually indicate the real-time temperature (using thermocouple 112). The vaporizable substance application apparatus 100 may enable the user 108 to precisely measure the temperature of a heated surface 200 (e.g., banger 104) and ensure the ideal temperature range (e.g., ideal state 402) for inhalation of the vaporized substance (e.g., vaporizable substance 202), according to one embodiment.

The vaporizable substance application apparatus 100 may include an applicator 116, a thermocouple 112, and a temperature indicator 114. The vaporizable substance application apparatus 100 may have the thermocouple 112 at a second end 111B of the apparatus (e.g., vaporizable substance application apparatus 100) to measure the temperature of any surface (e.g., banger 104 and/or heated surface 200) upon contact. Further, the vaporizable substance application apparatus 100 may have the applicator 116 at a first end 111A to apply the extracts (e.g., vaporizable substance 202) on the heated surface 200, according to one embodiment.

The vaporizable substance application apparatus 100 may be communicatively coupled to a mobile device 500 of the user 108 through a short-range communication network 308. The vaporizable substance application apparatus 100 may communicate a usage data (e.g., frequency of use and/or temperature measured) of the vaporizable substance application apparatus 100 to the coupled mobile device 500. The vaporizable substance application apparatus 100 may further include a haptic indicator 304 and a chime indicator 306, according to one embodiment.

The dab rig 102 may be a specific type of inbreathing apparatus to enable the user 108 to inhale a vaporized substance 202 (e.g., medicinal plant resin, a botanical and/or essential oil) for medicinal and/or therapeutic treatment. In another embodiment, the dab rig 102 may enable the user 108 to inhale a vaporizable drug and/or a concentrate such as wax, shatter, BHO, CO2 oil, and/or other *cannabis* concentrates, according to one embodiment.

The banger 104 may be a small, circular-shaped dish used as an attachment for the dab rig 102. The banger 104 may be made up of titanium, quartz and/or ceramic material. The banger 104 may be removably attached to the dab rig 102. The banger 104 may be heated (e.g., using blow torch 106) to an extremely high temperature and used to vaporize extracts (e.g., vaporizable substance 202). The real-time temperature of the banger 104 may be measured using the thermocouple 112 of the vaporizable substance application apparatus 100, according to one embodiment.

The blow torch 106 may be a fuel-burning tool to produce a hot flame to heat and raise the temperature of the banger 104 to an ideal state 402. The blow torch 106 may be filled with butane gas. The blow torch 106 may heat the banger 104 surface approximately up to 1000 degree Fahrenheit, according to one embodiment.

The user 108 may be an individual (e.g., a patient) who wishes to inhale the vaporized substance (e.g., vaporizable substance 202) at the ideal temperature (e.g., ideal state 402) to get the desired experience. The user 108 may heat the banger 104 surface of the dab rig 102 using the blow torch 106. The user 108 may be able to observe the real-time temperature on the temperature indicator 114 of the vaporizable substance application apparatus 100. The user 108 may be notified (e.g., when display module 300 illuminates in second color) by the vaporizable substance application apparatus 100 when the optimal temperature (e.g., ideal state 402) has reached, according to one embodiment.

The user 108 may apply the vaporizable substance 202 onto the heated surface 200 using the applicator 116 of the vaporizable substance application apparatus 100. In another embodiment, the user 108 may have a mobile device 500 communicatively coupled with the vaporizable substance application apparatus 100 to receive a usage data (e.g., frequency of use and/or temperature measured) of the vaporizable substance application apparatus 100, according to one embodiment.

Figure 1B:
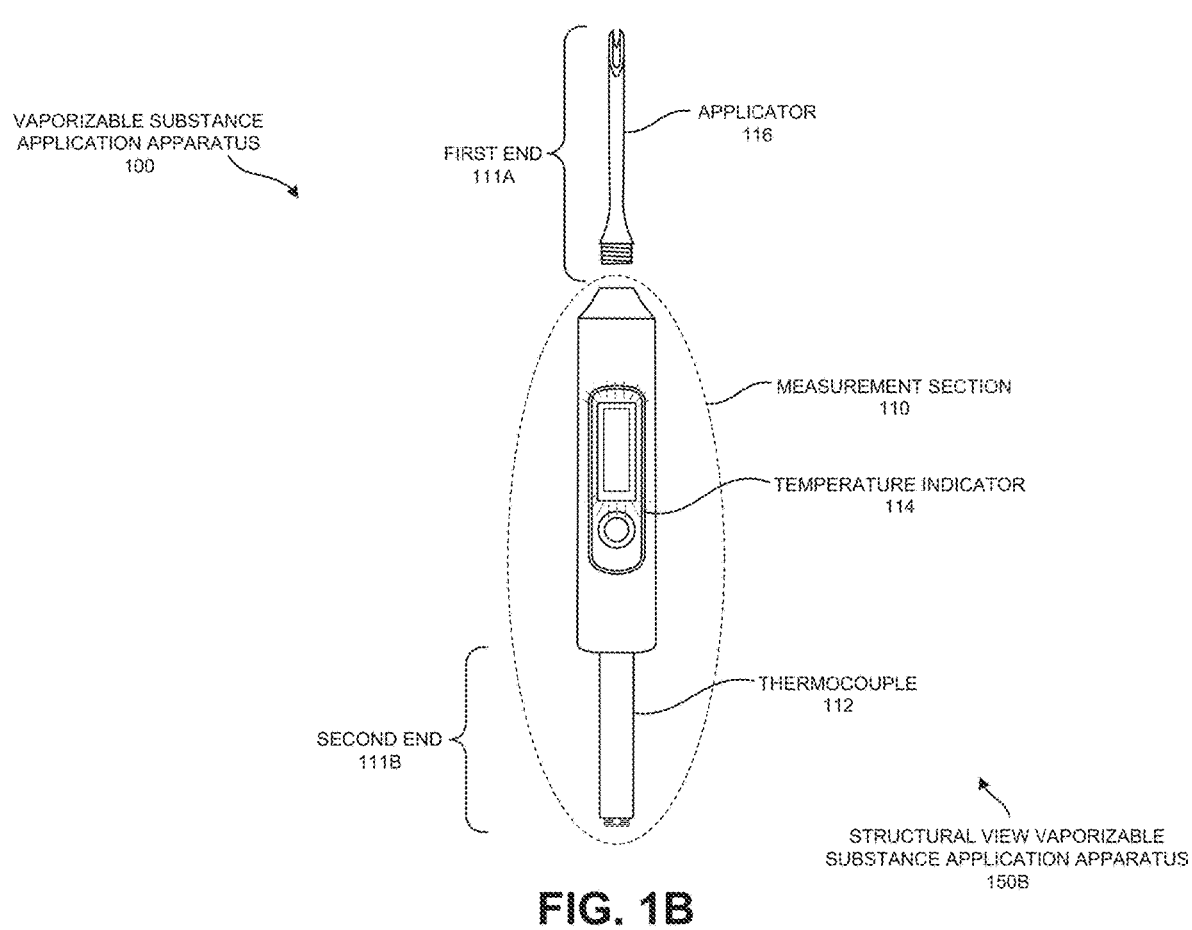
FIG. 1B is a structural view of the vaporizable substance application apparatus of FIG. 1A, according to one or more embodiments.

FIG. 1B is a structural view 150B of the vaporizable substance application apparatus 100 of FIG. 1A, according to one embodiment. Particularly, FIG. 1B illustrates a measurement section 110, a first end 111A, a second end 111B, a thermocouple 112, a temperature indicator 114, and an applicator 116, according to one embodiment.

The measurement section 110 may be a temperature evaluation unit for measuring and indicating the real-time temperature. The measurement section 110 may be comprised of the temperature indicator 114 and the thermocouple 112. The measurement section 110 may have the thermocouple 112 removably attached on the second end 111B to capture the real-time temperature, according to one embodiment.

The measurement section 110 may have a fitting slot on the first end 111A to enable the user 108 to attach the applicator 116 to the measurement section 110. In another embodiment, the measurement section 110 of the vaporizable substance application apparatus 100 may be able to attach different types of applicators (e.g., applicator 116) on the first end 111A, according to one embodiment.

The thermocouple 112 may be a temperature sensor to capture the real-time temperature of the surface (e.g., banger 104 and/or heated surface 200) upon contact. The thermocouple 112 may be positioned on the second end 111B of the vaporizable substance application apparatus 100. The thermocouple 112 may be coupled to the temperature indicator 114 to display the captured temperature on the display screen of the temperature indicator 114. The thermocouple 112 may be capable of capturing the temperature from zero degrees Fahrenheit to 1000 degrees Fahrenheit. In another embodiment, the vaporizable substance application apparatus 100 may have a laser and/or an infrared temperature sensor to capture the real-time temperature, according to one embodiment.

The temperature indicator 114 may be a device that displays a captured temperature value and/or a change in temperature states (e.g., first state 400, second state 402, and third state 404). The temperature indicator 114 is positioned between the applicator 116 and the thermocouple 112 of the vaporizable substance application apparatus 100. The temperature indicator 114 may include a display module 300, a LED indicator 302, a haptic indicator 304, a chime indicator 306, and a short range communication circuitry 308, according to one embodiment.

The temperature indicator 114 may be coupled to the thermocouple 112 to communicate the real-time temperature. The temperature indicator 114 may have the display module 300 to show the captured temperature value. The background of the display module 300 of the temperature indicator 114 may illuminate in a plurality of colors (e.g., blue, green, red) to visually indicate the different temperature states (e.g., first state 400, second state 402, and third state 404). The temperature indicator 114 may display the room temperature when the thermocouple 112 is not in contact with any surface, according to one embodiment.

The applicator 116 may be a dab tool to enable the user 108 to expose the vaporizable substance 202 onto the heated surface 200. The applicator 116 is positioned on the first end 111A of the vaporizable substance application apparatus 100. The applicator 116 may be removably attached to the measurement section 110 of the vaporizable substance application apparatus 100, according to one embodiment.

Figure 2:
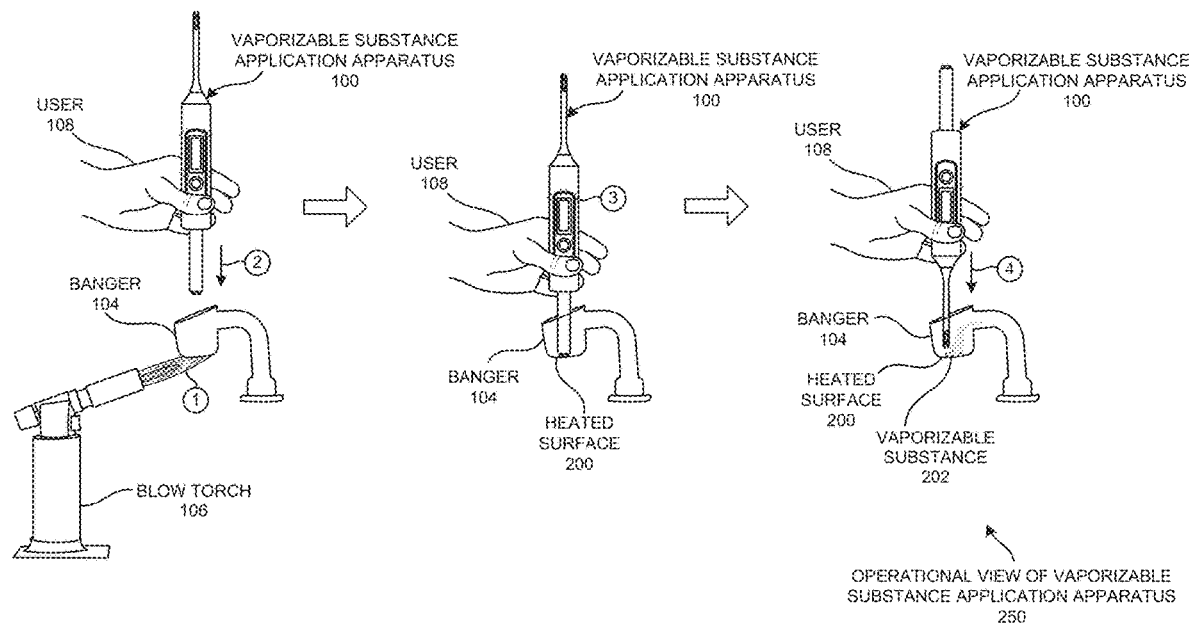
FIG. 2 is an operational view of the vaporizable substance application apparatus of FIG. 1A to illustrate the various stages of operation of the vaporizable substance application apparatus, according to one or more embodiments.

FIG. 2 is an operational view 250 of the vaporizable substance application apparatus 100 of FIG. 1A to illustrate the various stages of operation of the vaporizable substance application apparatus 100, according to one embodiment. Particularly, FIG. 2 illustrates a heated surface 200, and a vaporizable substance 202, according to one embodiment.

The heated surface 200 may be an exterior of the banger 104 when the heat is applied (e.g., using blow torch 106) to the banger 104. The heated surface 200 may enable the vaporizable substance 202 to aerify when the vaporizable substance 202 is placed on the heated surface 200. The heated surface 200 may have temperature up to and/or more than 1000 degrees Fahrenheit, according to one embodiment.

The vaporizable substance 202 may be a plant resin, a botanical oil, and/or an essential oil. The vaporizable substance 202 may get aerified when the vaporizable substance 202 is placed on the heated surface 200 to inhale through the dab rig 102. The vaporizable substance 202 may get aerified at a certain temperature range (e.g., ideal state 402). The vaporizable substance 202 may be more advantageous when inhaled at the ideal temperature state (e.g., ideal state 402). The vaporizable substance 202 may get combusted if the vaporizable substance 202 is exposed on the heated surface 200 at a temperature above the ideal state 402, according to one embodiment.

Further, the vaporizable substance 202 may not aerify if the vaporizable substance 202 is exposed on the heated surface 200 at a temperature below the ideal state 402. In another embodiment, the vaporizable substance 202 may be a vaporizable drug and/or a concentrate such as wax, shatter, BHO, CO2 oil, and/or other *cannabis* concentrates, according to one embodiment.

FIG. 2 illustrates the number of operations between the blow torch 106, the banger 104, and the vaporizable substance application apparatus 100. Particularly, circle '2' of FIG. 2 illustrates the banger 104 being heated to an extremely high temperature using the blow torch 106. The circle '2' shows the vaporizable substance application apparatus 100 being inserted (e.g., from thermocouple 112 end) in the banger 104 to measure the surface temperature of the heated banger (e.g., heated surface 200). The circle '3' shows the vaporizable substance application apparatus 100 indicating the ideal temperature state (e.g., ideal state 402) of the heated banger surface (e.g., heated surface 200). The circle '4' shows the vaporizable substance 202 being applied onto the heated surface 200 (e.g., from applicator 116 end) when the vaporizable substance application apparatus 100 visually indicates the ideal state 402, according to one embodiment.

Figure 3:
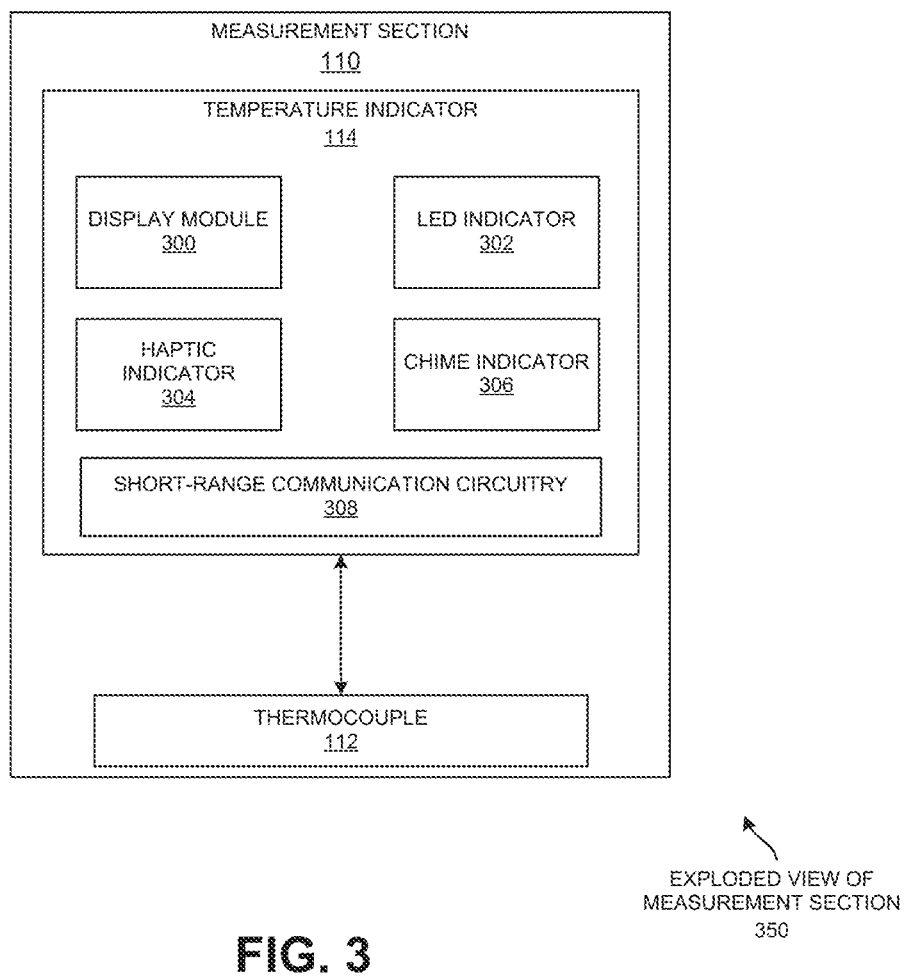
FIG. 3 is an exploded view of a measurement section of the vaporizable substance application apparatus of FIG. 1A, according to one or more embodiments.

FIG. 3 is an exploded view 300 of the measurement section 110 of the vaporizable substance application apparatus 100 of FIG. 1A, according to one embodiment. Particularly, FIG. 3 illustrates a display module 300, a LED indicator 302, a haptic indicator 304, a chime indicator 306, and a short-range communication circuitry 308, according to one embodiment.

The display module 300 may be an LCD screen of the temperature indicator 114 of the measurement section 110 to show the real-time temperature captured through the thermocouple 112. The background of the display module 300 may illuminate in a plurality of colors (e.g., blue, green, red) to visually indicate the different temperature ranges (e.g., first state 400, second state 402, and third state 404). The display module 300 may indicate a first state 400, a second state 402, and/or a third state 404 to show the range (e.g., temperature range) of the captured temperature, according to one embodiment.

The background of the display module 300 may illuminate in a first color (e.g., blue) to indicate that the captured temperature is below the ideal range (e.g., ideal state 402). The background of the display module 300 may illuminate in a second color (e.g., green) to indicate that the captured temperature is within the ideal range (e.g., ideal state 402). The background of the display module 300 may illuminate in a third color (e.g., red) to indicate that the captured temperature exceeds the ideal range (e.g., ideal state 402), according to one embodiment.

The LED indicator 302 may be coupled with the display module 300 of the temperature indicator 114 to enable the display module 300 to illuminate in a plurality of colors (e.g., blue, green, red) to visually indicate the captured temperature range (e.g., first state 400, second state 402, and third state 404). The LED indicator 302 may enable the display module 300 to illuminate in blue, green, and/or red color. The LED indicator 302 may be programmable to illuminate in a particular color for corresponding temperature range, according to one embodiment.

The haptic indicator 304 may be an electronic circuitry of the vaporizable substance application apparatus 100 configured to vibrate when the captured temperature is in the ideal temperature state (e.g., ideal state 402). The haptic indicator 304 may be located in the temperature indicator 114 of the vaporizable substance application apparatus 100. The haptic indicator 304 of the temperature indicator 114 may be coupled with the display module 300 and/or the thermocouple 112 to enable the vaporizable substance application apparatus 100 to vibrate when the captured temperature is in the ideal temperature state (e.g., ideal state 402), according to one embodiment.

The chime indicator 306 may be a small musical instrument (e.g., in the temperature indicator 114) configured to make a clear ringing sound when the captured temperature is in the ideal temperature state (e.g., ideal state 402). The chime indicator 306 of the temperature indicator 114 may be coupled with the display module 300 and/or the thermocouple 112 to enable the vaporizable substance application apparatus 100 to make an audible noise when the captured temperature is in the ideal temperature state (e.g., ideal state 402). The chime indicator 306 may be programmed with a ringtone and/or an audio clip when the vaporizable substance application apparatus 100 paired to the mobile device 500 through the short-range communication circuitry 308, according to one embodiment.

The short-range communication circuitry 308 may be a communication module to enable the vaporizable substance application apparatus 100 to establish a wireless connection with the mobile device 500 of the user 108. The short-range communication circuitry 308 may communicate a usage data (e.g., a frequency of use of the apparatus, a temperature measured at the time of application) of the vaporizable substance application apparatus 100 to the communicatively coupled mobile device 500 through the short range communication network 308. The short-range communication circuitry 308 may be a Bluetooth® module, a ZigBee Module® and/or an Infrared Module® etc., according to one embodiment.

Figure 4:
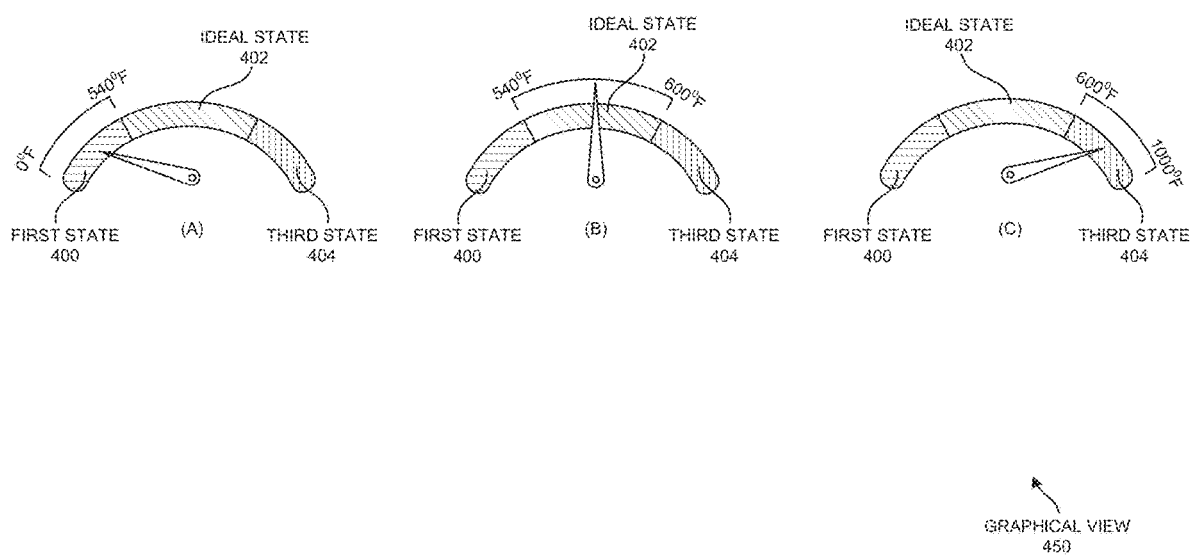
FIG. 4 is a graphical view illustrating illumination of a temperature indicator of the vaporizable substance application apparatus of FIG. 1A for different temperature range, according to one or more embodiments.

FIG. 4 is a graphical view 450 illustrating illumination of the temperature indicator 114 of the vaporizable substance application apparatus 100 of FIG. 1A for different temperature range (e.g., first state 400, ideal state 402, and third state 404), according to one embodiment. Particularly, FIG. 4 illustrates a first state 400, an ideal state 402 and a third state 404, according to one embodiment.

The first state 400 may be a predefined temperature range that is insufficient to aerify the vaporizable substance 202 for inhalation. The first state 400 may be approximately between 0 degrees Fahrenheit and 540 degrees Fahrenheit. In the first state 400 of the vaporizable substance application apparatus 100, the background of the display module 300 (e.g., of temperature indicator 114) may illuminate in the first color (e.g., blue light), according to one embodiment.

The ideal state 402 (e.g., second state) may be a predefined temperature range for applying the vaporizable substance 202 onto the heated surface 200 to get the desired experience of the inhalation of the vaporized substance (e.g., vaporizable substance 202). The ideal state 402 of the vaporizable substance application apparatus 100 may be predefined by the manufacturer. The ideal state 402 may be approximately between 540 degrees Fahrenheit and 600 degrees Fahrenheit. In the ideal state 402 of the vaporizable substance application apparatus 100, the background of the display module 300 (e.g., of temperature indicator 114) may illuminate in the second color (e.g., green light). In another embodiment, the ideal state 402 of the vaporizable substance application apparatus 100 may be adjusted by the user 108 through the communicatively coupled mobile device 500, according to one embodiment.

The third state 404 may be an excess temperature range that may combust the vaporizable substance 202. The third state 404 may be approximately between 600 degrees Fahrenheit and 1000 degrees Fahrenheit. In the third state 404 of the vaporizable substance application apparatus 100, the background of the display module 300 (e.g., of temperature indicator 114) may illuminate in the third color (e.g., red light), according to one embodiment.

FIG. 4 illustrates different temperature states (e.g., first state 400, ideal state 402, and third state 404) captured using the vaporizable substance application apparatus 100. Particularly, the graphical indicator shown in circle 'A' of FIG. 4 illustrates the temperature captured by the vaporizable substance application apparatus 100 is in the first state 400 (e.g., temperature between 0 degrees Fahrenheit and 540 degrees Fahrenheit). The temperature being in the first state 400 enables the temperature indicator 114 of the vaporizable substance application apparatus 100 to illuminate in the first color (e.g., blue color), according to one embodiment.

The graphical indicator shown in circle 'B' of FIG. 4 illustrates the temperature captured by the vaporizable substance application apparatus 100 is in the second state and/or the ideal state 402 (e.g., temperature between 540 degrees Fahrenheit and 600 degrees Fahrenheit). The temperature being in the ideal state 402 enables the temperature indicator 114 of the vaporizable substance application apparatus 100 to illuminate in the second color (e.g., green color), according to one embodiment.

The graphical indicator shown in circle 'C' of FIG. 4 illustrates the temperature captured by the vaporizable substance application apparatus 100 is in the third state 404 (e.g., temperature between 600 degrees Fahrenheit and 1000 degrees Fahrenheit). The temperature being in the third state 404 enables the temperature indicator 114 of the vaporizable substance application apparatus 100 to illuminate in the third color (e.g., red color), according to one embodiment.

Figure 5A:
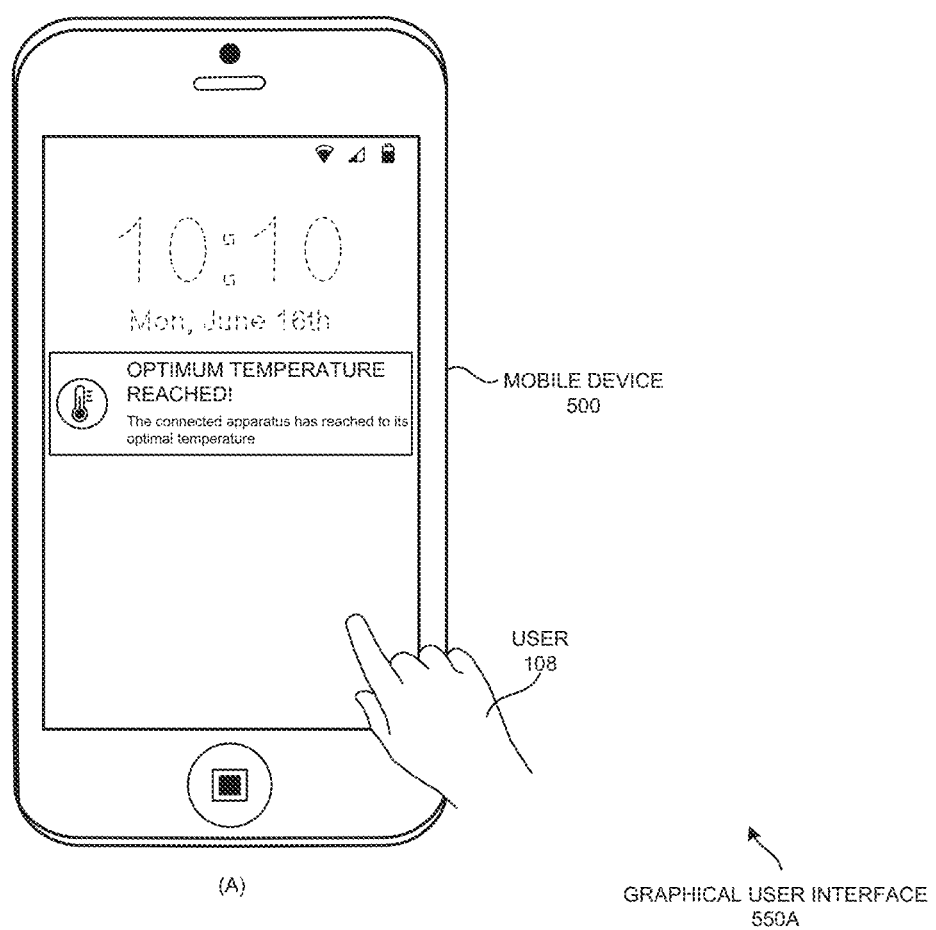
FIG. 5A is a user interface view displaying a notification communicated through the vaporizable substance application apparatus of FIG. 1A to a communicatively coupled mobile device of the user, according to one or more embodiments.

FIG. 5A is a user interface view 550A displaying a notification communicated through the vaporizable substance application apparatus 100 of FIG. 1A to a communicatively coupled mobile device 500 of the user 108, according to one embodiment. Particularly, FIG. 5 illustrates a mobile device 500, according to one embodiment.

The mobile device 500 may be a network enabled computing device communicatively coupled to the vaporizable substance application apparatus 100 through a short range communication network 308. The mobile device 500 may receive a notification through the short-range communication circuitry 308 of the vaporizable substance application apparatus 100 when the optimal temperature (e.g., ideal state 402) has reached, according to one embodiment.

Further, the mobile device 500 may receive a usage data (e.g., a frequency of use of the apparatus, a temperature measured at the time of application) of the vaporizable substance application apparatus 100. The mobile device 500 may enable the user 108 to manage the programmable properties of the ideal state 402, the chime indicator 306, and the haptic indicator 304 of the vaporizable substance application apparatus 100. The mobile device 500 may be a mobile phone, a personal computer, a tab, a laptop and/or any other network-enabled computing device, according to one embodiment.

The user interface 'A' of FIG. 5A illustrates the user 108 receiving notification on the mobile device 500 communicated through the short-range communication circuitry 308 of the vaporizable substance application apparatus 100 when the optimal temperature (e.g., ideal state 402) has reached. The received notification may provide the real-time temperature information captured using the vaporizable substance application apparatus 100, according to one embodiment.

Figure 5B:
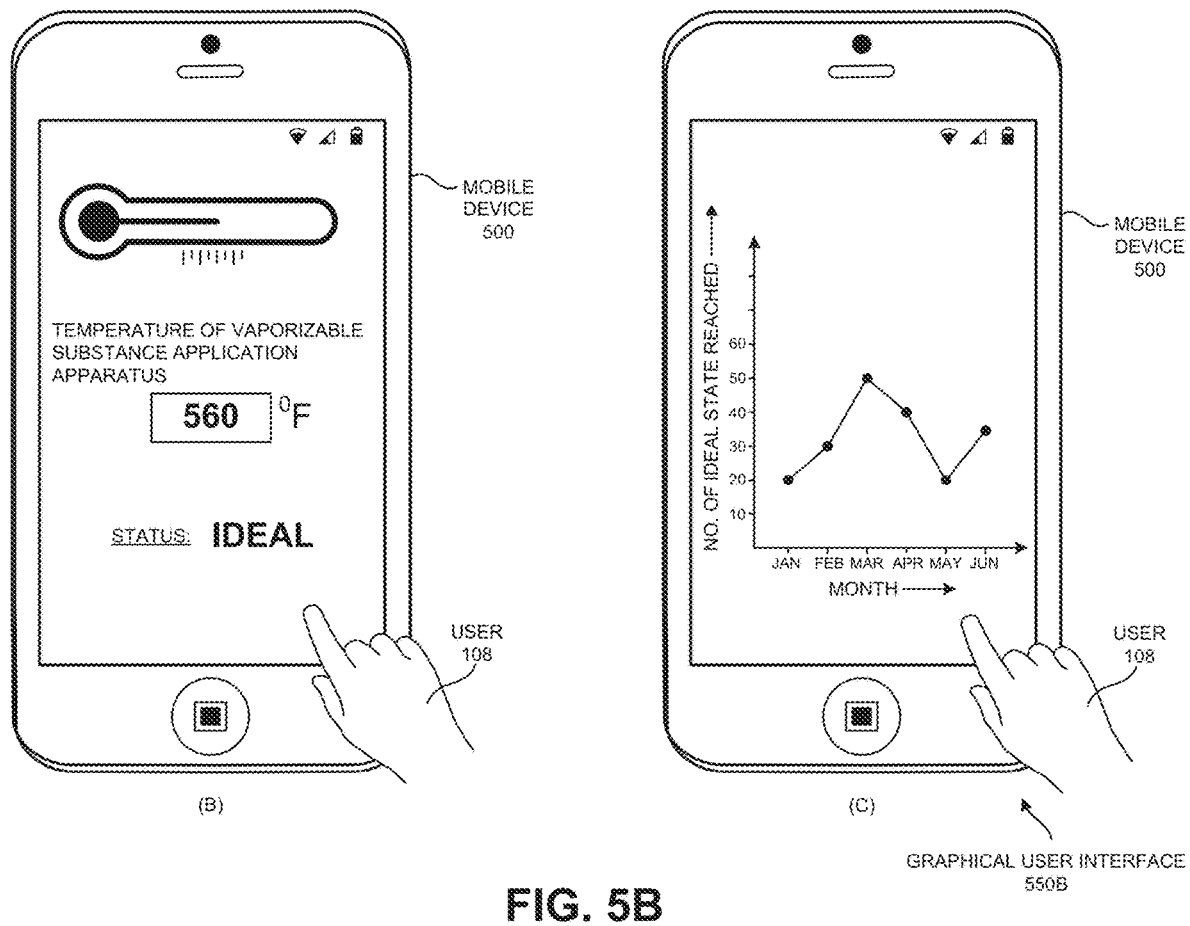
FIG. 5B is another user interface view displaying a real-time statistics and a usage data history of the vaporizable substance application apparatus of FIG. 1A received by the mobile device of the user, according to one or more embodiments.

FIG. 5B is another user interface view 550B displaying a real-time statistics and a usage data history of the vaporizable substance application apparatus 100 of FIG. 1A received by the mobile device 500 of the user 108, according to one embodiment.

The user interface 'B' of FIG. 5B illustrates the user 108 receiving real-time temperature and the status of the vaporizable substance application apparatus 100 on the mobile device 500. The user interface 'C' of FIG. 5B graphically illustrates the usage data of the vaporizable substance application apparatus 100 with the ideal state 402 for a particular time period. In another embodiment, the user 108 may receive the usage data related to the temperature measured at the time of application of the vaporizable substance 202, and a temperature decay pattern on the mobile device 500, according to one embodiment.

An example embodiment will now be described. John Doe may be working as a software engineer in ACME Software Company in the United States of America. John may have been suffering from migraine causing him recurrent headaches at any moment resulting in regular disturbances in his office work and/or regular activities. John may have been prescribed a therapeutic medicine to treat his migraines that requires inhalation of vaporized botanical oil. John may have to heat the surface (e.g., made of quartz, ceramic, and/or titanium) to an ideal temperature prior to applying the botanical oil to the heated surface. John may have to use a stopwatch to ensure that the heated surface is not extremely hot and/or cold. However, this method may not help John to get the desired experience of inhalation to recover from his migraine problem.

John Doe may have been advised by his friend to use the vaporizable substance application apparatus 100 having the integrated ideal temperature indicator 114 as described in the various embodiments of FIGS. 1-5B to vaporize the botanical oil (e.g., vaporizable substance 202) at the ideal temperature (e.g., ideal state 402). John Doe may have used the vaporizable substance application apparatus 100 having the integrated ideal temperature indicator 114 as described in the various embodiments of FIGS. 1-5B and found it to be very useful.

John may not have to use a stopwatch now. John may now be able to heat the surface (e.g., banger 104) and observe the real-time temperature on the temperature indicator 114 (e.g., display module 300) of the vaporizable substance application apparatus 100 as described in the various embodiments of FIGS. 1A-5B by contacting the thermocouple 112 to the heated surface 200. Further, the illuminating background (e.g., of display module 300) of the temperature indicator 114 as described in the various embodiments of FIGS. 1A-5B may have helped John to observe the temperature states of the heated surface 200. John may apply the prescribed essential oil (e.g., vaporizable substance 202) onto the heated surface 200 using the applicator 116 of the vaporizable substance application apparatus 100 as described in the various embodiments of FIGS. 1A-5B when the temperature is in the ideal state 402.

John may now be able to more efficiently apply a heating and cooling procedure to unlock the therapeutic properties of the prescription drug through the vaporizable substance application apparatus 100 having the integrated ideal temperature indicator 114 as described in the various embodiments of FIGS. 1A-5B. The various embodiments of FIGS. 1A-5B of the vaporizable substance application apparatus 100 having the integrated ideal temperature indicator 114 may have helped John to recover and feel better from his migraine and perform his office work and/or regular activities.

Although the present embodiments have been described with reference to specific example embodiments, it will be evident that various modifications and changes may be made to these embodiments without departing from the broader spirit and scope of the various embodiments. Accordingly, the specification and/or drawings may be regarded in an illustrative rather than a restrictive sense.

What is claimed is:

1. An apparatus, comprising:
    an applicator on a first end of the apparatus to apply a vaporizable substance onto a surface of a banger external to the apparatus, the surface of the banger configured to have heat applied thereto to enable the vaporizable substance applied thereon to aerify;
    a thermocouple on a second end of the apparatus configured to capture a real-time temperature of the surface of the banger upon contact therewith; and
    a temperature indicator positioned in between the applicator and the thermocouple, and coupled to both the applicator and the thermocouple,
        wherein the temperature indicator is configured to visually indicate:
            a first state in which a background of the temperature indicator is in a first color when the captured real-time temperature of the surface of the banger is below an ideal range,
            a second state in which the background of the temperature indicator is in a second color when the captured real-time temperature of the surface of the banger is within the ideal range, and
            a third state in which the background of the temperature indicator is in a third color when the captured real-time temperature of the surface of the banger exceeds the ideal range.

2. The apparatus of claim 1, wherein the vaporizable substance is at least one of a plant resin, a botanical oil, and an essential oil.

3. The apparatus of claim 1, wherein the ideal range is between approximately 540 degrees Fahrenheit and 600 degrees Fahrenheit.

4. The apparatus of claim 1, wherein the first color is blue, wherein the second color is green, and wherein the third color is red.

5. The apparatus of claim 1, further comprising a measurement section comprising the temperature indicator and the thermocouple,
wherein the applicator is removably attached to the measurement section of the apparatus.

6. The apparatus of claim 5, wherein different types of applicators are attachable to the measurement section of the apparatus.

7. The apparatus of claim 5, further comprising:
a short-range communication circuitry in the measurement section to communicate at least one of: a frequency of use of the apparatus and a temperature measured at a time of application of the vaporizable substance onto the surface of the banger using the applicator to a mobile device communicatively coupled with the apparatus.

8. The apparatus of claim 7, wherein the temperature indicator further comprises:
a haptic indicator to vibrate the apparatus when the captured real-time temperature of the surface of the banger is in the ideal range; and
a chime indicator to make an audible noise when the captured real-time temperature of the surface of the banger is in the ideal range, and
wherein the chime indicator is programmable with at least one of a ringtone and an audio clip when paired to the mobile device through the short-range communication circuitry.

9. A dabbing tool, comprising:
an applicator on a first end of the dabbing tool to apply a vaporizable substance onto a surface of a banger external to the dabbing tool, the surface of the banger configured to have heat applied thereto to enable the vaporizable substance applied thereon to aerify,
wherein the vaporizable substance is at least one of a plant resin, a botanical oil, and an essential oil;
a thermocouple on a second end of the dabbing tool configured to capture a real-time temperature of the surface of the banger upon contact therewith; and
a temperature indicator positioned in between the applicator and the thermocouple, and coupled to both the applicator and the thermocouple,
wherein the temperature indicator is configured to visually indicate:
a first state in which a background of the temperature indicator is in a first color when the captured real-time temperature of the surface of the banger is below an ideal range,
a second state in which the background of the temperature indicator is in a second color when the captured real-time temperature of the surface of the banger is within the ideal range, and
a third state in which the background of the temperature indicator is in a third color when the captured real-time temperature of the surface of the banger exceeds the ideal range,
wherein the ideal range is between approximately 540 degrees Fahrenheit and 600 degrees Fahrenheit.

10. The dabbing tool of claim 9, wherein the first color is blue, wherein the second color is green, and wherein the third color is red.

11. The dabbing tool of claim 9, further comprising a measurement section comprising the temperature indicator and the thermocouple,
wherein the applicator is removably attached to the measurement section of the dabbing tool.

12. The dabbing tool of claim 11, wherein different types of applicators are attachable to the measurement section of the dabbing tool.

13. The dabbing tool of claim 11, further comprising:
a short-range communication circuitry in the measurement section to communicate at least one of: a frequency of use of the dabbing tool and a temperature measured at a time of application of the vaporizable substance onto the surface of the banger using the applicator to a mobile device communicatively coupled with the dabbing tool.

14. The dabbing tool of claim 13, wherein the temperature indicator further comprises:
a haptic indicator to vibrate the dabbing tool when the captured real-time temperature of the surface of the banger is in the ideal range; and
a chime indicator to make an audible noise when the captured real-time temperature of the surface of the banger is in the ideal range, and
wherein the chime indicator is programmable with at least one of a ringtone and an audio clip when paired to the mobile device through the short-range communication circuitry.

15. An apparatus, comprising:
an applicator on a first end of the apparatus to apply a vaporizable substance onto a surface of a banger external to the apparatus, the surface of the banger configured to have heat applied thereto to enable the vaporizable substance applied thereon to aerify; and
a measurement section comprising:
a thermocouple on a second end of the apparatus configured to capture a real-time temperature of the surface of the banger upon contact therewith; and
a temperature indicator positioned in between the applicator and the thermocouple, and coupled to both the applicator and the thermocouple,
wherein the temperature indicator is configured to visually indicate:
a first s to e in which a background of the temperature indicator is in a first color when the captured real-time temperature of the surface of the banger is below an ideal range,
a second state in which the background of the temperature indicator is in a second color when the captured real-time temperature of the surface of the banger is within the ideal range, and
a third state in which the background of the temperature indicator is in a third color when the captured real-time temperature of the surface of the banger exceeds the ideal range,
wherein the ideal range is between approximately 540 degrees Fahrenheit and 600 degrees Fahrenheit, and
wherein the applicator is removably attached to the measurement section of the apparatus.

16. The apparatus of claim 15, wherein the vaporizable substance is at least one of a plant resin, a botanical oil, and an essential oil.

17. The apparatus of claim 15, wherein the first color is blue, wherein the second color is green, and wherein the third color is red.

18. The apparatus of claim 15, wherein different types of applicators are attachable to the measurement section of the apparatus.

19. The apparatus of claim 15, further comprising:
- a short-range communication circuitry in the measurement section to communicate at least one of: a frequency of use of the apparatus and a temperature measured at a time of application of the vaporizable substance onto the surface of the banger using the applicator to a mobile device communicatively coupled with the apparatus.

20. The apparatus of claim 19, wherein the temperature indicator further comprises:
- a haptic indicator to vibrate the apparatus when the captured real-time temperature of the surface of the banger is in the ideal range; and
- a chime indicator to make an audible noise when the captured real-time temperature of the surface of the banger is in the ideal range,
- wherein the chime indicator is programmable with at least one of a ringtone and an audio clip when paired to the mobile device through the short-range communication circuitry.

* * * * *